United States Patent
Maschino et al.

(10) Patent No.: US 10,570,540 B2
(45) Date of Patent: *Feb. 25, 2020

(54) METHOD FOR MAKING HYDROFORMED EXPANDED SPUN BONDED NONWOVEN WEB

(71) Applicant: TREDEGAR FILM PRODUCTS CORPORATION, Richmond, VA (US)

(72) Inventors: Andrew D. Maschino, Paris, IL (US); Michael Estel Fisher, Rosedale, IN (US); John Richard Renner, Marshall, IL (US); Todd R. Skochdopole, Moseley, VA (US)

(73) Assignee: TREDEGAR FILM PRODUCTS CORPORATION, Richmond, VA (US)

( * ) Notice: Subject to any disclaimer, the term of this patent is extended or adjusted under 35 U.S.C. 154(b) by 1 day.

This patent is subject to a terminal disclaimer.

(21) Appl. No.: 15/833,363

(22) Filed: Dec. 6, 2017

(65) Prior Publication Data

US 2018/0094370 A1    Apr. 5, 2018

Related U.S. Application Data

(62) Division of application No. 15/248,762, filed on Aug. 26, 2016, now Pat. No. 9,856,589.
(Continued)

(51) Int. Cl.
*B26F 1/26* (2006.01)
*D04H 1/46* (2012.01)
(Continued)

(52) U.S. Cl.
CPC ......... *D04H 1/46* (2013.01); *A61F 13/15699* (2013.01); *A61F 13/5116* (2013.01);
(Continued)

(58) Field of Classification Search
CPC ................... B26F 1/26; B29C 37/0053; B29C 2793/0045; D04H 3/11
(Continued)

(56) References Cited

U.S. PATENT DOCUMENTS

| | | |
|---|---|---|
| 3,485,706 A | 12/1969 | Evans |
| 3,493,462 A | 2/1970 | Bunting, Jr. et al. |

(Continued)

FOREIGN PATENT DOCUMENTS

| | | |
|---|---|---|
| CN | 1446278 A | 9/2006 |
| CN | 101511579 A | 8/2009 |

(Continued)

OTHER PUBLICATIONS

Invitation to Pay Additional Fees dated Oct. 11, 2016, for International Patent Application No. PCT/US2016/048980.
(Continued)

*Primary Examiner* — Leo B Tentoni
(74) *Attorney, Agent, or Firm* — Karceski IP Law, PLLC

(57) ABSTRACT

A method for hydroforming a spun bonded nonwoven web includes applying a plurality of pressurized liquid jets onto an original unexpanded spun bonded nonwoven web having an original loft while the web passes over a forming structure. A plurality of spun bonded fibers in the original unexpanded spun bonded nonwoven web are reoriented from a closely packed substantially horizontal orientation to a more loosely packed orientation with greater vertical spacing between the fibers to produce a hydroformed expanded spun bonded nonwoven web having a loft of at least about 1.3 times greater than the original loft of the original unexpanded spun bonded nonwoven web, and an air permeability of at least about 1.2 times greater than an original air permeability of the original unexpanded spun bonded nonwoven web. The hydroformed expanded spun
(Continued)

bonded nonwoven web has a surface with a plurality of protuberances in a pattern corresponding to the pattern of apertures in the forming structure.

7 Claims, 12 Drawing Sheets

Related U.S. Application Data

(60) Provisional application No. 62/348,343, filed on Jun. 10, 2016.

(51) Int. Cl.

| | | |
|---|---|---|
| B29C 48/00 | (2019.01) | |
| B29C 48/08 | (2019.01) | |
| B29C 37/00 | (2006.01) | |
| A61F 13/511 | (2006.01) | |
| A61F 13/15 | (2006.01) | |
| D04H 1/492 | (2012.01) | |
| D04H 1/732 | (2012.01) | |
| D04H 3/011 | (2012.01) | |
| D04H 5/03 | (2012.01) | |
| D04H 5/08 | (2012.01) | |
| B32B 3/26 | (2006.01) | |
| B32B 3/30 | (2006.01) | |
| B32B 5/02 | (2006.01) | |
| B32B 7/12 | (2006.01) | |
| B32B 27/32 | (2006.01) | |
| B32B 37/10 | (2006.01) | |
| B32B 37/12 | (2006.01) | |
| B32B 37/24 | (2006.01) | |
| D04H 13/02 | (2006.01) | |
| B29L 31/48 | (2006.01) | |

(52) U.S. Cl.
CPC .... *A61F 13/51108* (2013.01); *B29C 37/0053* (2013.01); *B29C 48/002* (2019.02); *B29C 48/0021* (2019.02); *B29C 48/08* (2019.02); *B32B 3/266* (2013.01); *B32B 3/30* (2013.01); *B32B 5/022* (2013.01); *B32B 7/12* (2013.01); *B32B 27/32* (2013.01); *B32B 37/1009* (2013.01); *B32B 37/12* (2013.01); *B32B 37/24* (2013.01); *D04H 1/492* (2013.01); *D04H 1/732* (2013.01); *D04H 3/011* (2013.01); *D04H 5/03* (2013.01); *D04H 5/08* (2013.01); *D04H 13/02* (2013.01); *A61F 2013/15829* (2013.01); *A61F 2013/51169* (2013.01); *B29C 2793/0045* (2013.01); *B29K 2995/0068* (2013.01); *B29L 2031/4878* (2013.01); *B32B 2037/1072* (2013.01); *B32B 2262/0253* (2013.01); *B32B 2305/02* (2013.01); *B32B 2305/20* (2013.01); *B32B 2307/726* (2013.01); *B32B 2323/10* (2013.01); *B32B 2555/02* (2013.01); *Y10T 442/674* (2015.04); *Y10T 442/681* (2015.04)

(58) Field of Classification Search
USPC .......................... 264/103, 154, 163; 28/104
See application file for complete search history.

(56) References Cited

U.S. PATENT DOCUMENTS

| | | | |
|---|---|---|---|
| 3,531,363 A * | 9/1970 | Shambelan | D04H 3/10 28/111 |
| 4,024,612 A | 5/1977 | Contractor et al. | |
| 4,535,020 A | 8/1985 | Thomas et al. | |
| 4,591,523 A | 5/1986 | Thompson | |
| 4,609,518 A | 9/1986 | Curro et al. | |
| 4,629,643 A | 12/1986 | Curro et al. | |
| 4,695,422 A | 9/1987 | Curro et al. | |
| 4,704,112 A | 11/1987 | Suzuki et al. | |
| 4,759,297 A | 7/1988 | Calligarich | |
| 4,839,216 A | 6/1989 | Curro et al. | |
| 4,868,958 A | 9/1989 | Suzuki et al. | |
| 4,995,930 A | 2/1991 | Merz et al. | |
| 5,369,858 A | 12/1994 | Gilmore et al. | |
| 5,414,914 A | 5/1995 | Suzuki et al. | |
| 5,459,912 A * | 10/1995 | Oathout | D04H 1/495 28/104 |
| 5,520,875 A | 5/1996 | Wnuk et al. | |
| 5,635,275 A | 6/1997 | Biagioli et al. | |
| 5,674,211 A | 10/1997 | Ekdahl | |
| 5,733,628 A | 3/1998 | Pelkie | |
| 5,770,144 A | 6/1998 | James et al. | |
| 5,792,412 A | 8/1998 | Lee et al. | |
| 5,824,352 A | 10/1998 | Yang et al. | |
| 5,834,092 A | 11/1998 | Lee et al. | |
| 5,879,782 A | 3/1999 | Lee et al. | |
| 6,022,607 A | 2/2000 | James et al. | |
| 6,114,595 A | 9/2000 | Moore et al. | |
| 6,240,817 B1 | 6/2001 | James et al. | |
| 6,242,074 B1 | 6/2001 | Thomas | |
| 6,312,640 B1 | 11/2001 | Shimalla | |
| 6,321,425 B1 | 11/2001 | Putnam et al. | |
| 6,514,889 B1 | 2/2003 | Theoret et al. | |
| 6,548,731 B2 | 4/2003 | Mizutani et al. | |
| 6,562,170 B2 | 5/2003 | Thomas | |
| 6,660,361 B1 | 12/2003 | Shimalla | |
| 6,736,916 B2 | 5/2004 | Steinke et al. | |
| 6,849,319 B2 | 2/2005 | Cree et al. | |
| 7,144,831 B2 | 12/2006 | Carter et al. | |
| 7,204,907 B2 | 4/2007 | Cree et al. | |
| 7,364,687 B2 | 4/2008 | Maschino et al. | |
| 7,655,176 B2 | 2/2010 | Stone et al. | |
| 7,858,544 B2 | 12/2010 | Turi et al. | |
| 8,093,163 B2 | 1/2012 | Turi et al. | |
| 8,359,720 B2 | 1/2013 | Dorsey et al. | |
| 8,410,007 B2 | 4/2013 | Turi et al. | |
| 8,510,922 B2 | 8/2013 | Turi et al. | |
| 8,722,963 B2 | 5/2014 | Kanya et al. | |
| 8,841,507 B2 | 9/2014 | Kanya et al. | |
| 2001/0008180 A1 | 7/2001 | Anderson et al. | |
| 2002/0104609 A1 | 8/2002 | Thomas | |
| 2002/0150609 A1 | 10/2002 | Kono et al. | |
| 2003/0131454 A1* | 7/2003 | Noelle | D04H 1/067 28/104 |
| 2003/0181882 A1 | 9/2003 | Toyoshima et al. | |
| 2004/0227275 A1* | 11/2004 | Maschino | B26F 1/26 264/500 |
| 2005/0101216 A1 | 5/2005 | Middlesworth et al. | |
| 2006/0057921 A1 | 3/2006 | Turi et al. | |
| 2006/0087053 A1 | 4/2006 | O'Donnell et al. | |
| 2006/0259003 A1 | 11/2006 | Venkitaraman et al. | |
| 2007/0232178 A1 | 10/2007 | Polat et al. | |
| 2008/0300562 A1* | 12/2008 | Ahoniemi | D04H 3/11 604/367 |
| 2009/0068394 A1 | 3/2009 | Noelle et al. | |
| 2010/0048072 A1 | 2/2010 | Kauschke et al. | |
| 2010/0159774 A1 | 6/2010 | Chambers, Jr. et al. | |
| 2010/0247844 A1 | 9/2010 | Curro et al. | |
| 2011/0183109 A1 | 7/2011 | Seyler et al. | |
| 2011/0223388 A1 | 9/2011 | Stone et al. | |
| 2011/0250815 A1* | 10/2011 | Pourdeyhimi | D04H 3/11 28/104 X |
| 2012/0179125 A1 | 7/2012 | Kanya et al. | |
| 2012/0189814 A1 | 7/2012 | Coslett et al. | |
| 2012/0315225 A1 | 12/2012 | Porbeni et al. | |
| 2014/0259483 A1 | 9/2014 | Cheng et al. | |
| 2015/0148764 A1 | 5/2015 | Latimer et al. | |
| 2015/0267327 A1 | 9/2015 | Kanya | |

(56) References Cited

U.S. PATENT DOCUMENTS

FOREIGN PATENT DOCUMENTS

| | | |
|---|---|---|
| CN | 101670209 A | 3/2010 |
| CN | 101965253 A | 2/2011 |
| DE | 2161235 A1 | 7/1973 |
| DE | 10008827 A1 | 9/2001 |
| EP | 0209713 A2 | 1/1987 |
| EP | 0423619 A1 | 4/1991 |
| EP | 2159043 A2 | 3/2010 |
| EP | 2544644 | 9/2011 |
| JP | H10219568 A | 8/1998 |
| JP | 2002355271 A | 12/2002 |
| JP | 2004000465 A | 1/2004 |
| JP | 2004298322 A | 10/2004 |
| JP | 2008503323 A | 2/2008 |
| JP | 2013076185 A | 4/2013 |
| KR | 1020120127636 | 11/2012 |
| KR | 101229245 B1 | 2/2013 |
| WO | 9309741 | 5/1993 |
| WO | 9424354 | 10/1994 |
| WO | 03035955 A2 | 5/2003 |
| WO | 03060215 A1 | 7/2003 |
| WO | 2009112956 A2 | 9/2009 |

OTHER PUBLICATIONS

International Search Report and Written Opinion dated Jan. 5, 2017, for International Patent Application No. PCT/US2016/048980.
International Search Report and Written Opinion dated Sep. 6, 2017, for International Patent Application No. PCT/US2017/036784.
International Preliminary Report on Patentability dated Dec. 11, 2018, for International Patent Application No. PCT/US2017/036784.
International Preliminary Report on Patentability dated Dec. 11, 2018, for International Patent Application No. PCT/US2016/048980.
Korean Office Action dated Apr. 15, 2019 for Korean Patent Application No. 10-2019-7000398.
Extended European Search Report dated Jul. 4, 2019, for European Patent Application No. 16904821.2.
Extended European Search Report dated Jul. 8, 2019, for European Patent Application No. 17811092.0.
Japanese Office Action dated Jun. 27, 2019, for Japanese Patent Application No. 2018-564774.
Japanese Office Action dated Jun. 27, 2019, for Japanese Patent Application No. 2018-564761.
Korean Office Action dated Jun. 13, 2019, for Korean Patent Application No. 10-2019-7000431.
Chinese Office Action dated Sep. 29, 2019, for Chinese Patent Application No. 201780045307.5.

\* cited by examiner

METHOD FOR MAKING HYDROFORMED EXPANDED SPUN BONDED NONWOVEN WEB

CROSS-REFERENCE TO RELATED APPLICATIONS

This application is a divisional U.S. patent application Ser. No. 15/248,762, filed on Aug. 26, 2016, which claims the benefit of priority to U.S. Provisional Patent Application No. 62/348,343, filed on Jun. 10, 2016, the entire contents both of which are incorporated herein by reference.

FIELD

The present invention is directed to a hydroformed expanded spun bonded nonwoven web and a method for making a hydroformed expanded spun bonded nonwoven web.

BACKGROUND

Nonwoven materials are commonly used in absorptive devices, such as diapers and feminine napkins. Nonwoven materials are often used as topsheet components of such absorptive devices where it is desirable to achieve softness due to the contact of the topsheet with the skin of the wearer of the absorptive device. A ratio of high loft to total thickness of the nonwoven material often indicates softness, because the nonwoven material is compressible, which in turn renders a softness sensation to the wearer of the absorptive device that includes the nonwoven material. While relatively high loft nonwovens are perceived to be soft and cool when used against the skin, special processing is typically needed to achieve such characteristics, which may increase the cost of the product.

Fiber entanglement by injecting and withdrawing barbed needles is one known method for creating relatively high loft nonwoven materials, but the process is relatively slow and costly. A faster production method for generating high loft nonwoven materials is a spunlacing process for hydro-entanglement of loose fibers. The spunlacing process may create relatively high lofted soft nonwoven materials that are soft and cool to the touch by using high pressure water jets that are essentially in the shape and diameter of needles to hydro-entangle the fibers.

Spunlacing is a process of entangling a web of loose fibers on a porous belt or a moving perforated or patterned screen to form a sheet structure by subjecting the fibers to multiple rows of fine high-pressure jets of water. The spunlacing process uses an array of very fine high velocity water jets, essentially the diameters of needles, instead of barbed needles, to entangle the fibers in order gain web integrity while yielding a relatively high loft nonwoven material. The needle-like water jets are applied by a high pressure header, and the pressure may range from 2000 psi to over 8000 psi. The water needle jet holes are typically about 0.005 inch in diameter and a single header may include between about 30 and about 80 holes per inch in a row. Three to eight headers may be placed in a row that is aligned in the machine direction, and the web of untangled fibers may move in the machine direction on a perforated belt or screen-like material. A vacuum zone exists underneath the belt to extract the water. After the fibers are hydro-entangled into a web, the web may be dried and wound into a roll that can then be unwound when converted and used as a layer in an absorptive device. The spunlacing process generally does not lend itself to produce laminates with a film layer while the lofting is occurring because the high pressure and needle-like shape of the water jets may damage the film layer, and may possibly remove most or all of the film from the nonwoven layer.

Spun bonded nonwovens are less costly than spunlace nonwovens, but typically have much less loft and are often not as soft as other nonwoven materials. The spun bonded process for making a nonwoven web is known. In a so-called Reicofil system, polymer pellets are fed into an extruder that extrudes continuous fibers through a die with a plurality of small openings. The fibers are thinned or stretched and cooled as the polymer exits the die. The fibers are then spun to random positions by air currents provided by manifolds or other devices. After the fibers are spun, the fibers are randomly positioned on a moving belt made of open screen material to create a matt of spun fibers. Suction may be applied to ensure the entangled fibers lay flat in a substantially horizontal orientation and are essentially pinned on the moving screen.

The matt of entangled fibers may then be fed into a calendar roll nip, with one roll having a smooth surface and one roll having raised points in a pattern. Both rolls may be heated to a point above the melting point of the polymer in the fibers. The matt is compressed as the raised points compress the matt against the smooth roll. The heat and pressure applied to the matt creates bonded points that hold the fibers in place to create a spun bonded nonwoven web.

Nonwoven materials, whether created by spun bonded, air laid, carded, spun laced, hydro-entangled, or other processes, have a basis weight that defines the mass of the fibers contained therein (typically measured in grams) within a square area (typically measured in a square meter) so that the basis weight is measured in grams per square meter ("gsm"). In addition, all fibers have a thickness or diameter that is referred to as denier. A nonwoven material having fibers with a heavier denier and fewer fibers can have the same basis weight as a nonwoven material having fibers with a lighter, or thinner denier and many more fibers. Features such as loft (thickness), which is a distance measured from the top of the nonwoven web to the bottom of the nonwoven web, for a given mass of fibers may be manipulated by choosing a fiber denier and process technique for creating loft, while entangling or bonding the fiber web so the web will have tensile strength and web integrity. Unfortunately, the spun bonded process does not lend itself to producing higher lofted nonwovens due its tendency to have horizontal fibers.

The properties of spun bonded nonwovens may be manipulated by changing the denier and basis weight of the fibers, as well as changing the polymer(s) used to create the fibers. Some polymers are stiffer, such as polyesters, and some polymers are more flexible, such as polypropylene and polyethylene. Only recently have polyethylene polymers been created with enough draw down to be made into a fiber. Polypropylene is a common polymer used in spun bonded nonwovens and a spun bonded polypropylene nonwoven web is typically referred to as "SBPP".

It is also desirable for the fibers in the nonwovens to be used in topsheets for absorptive devices be hydrophilic. Natural cellulose fibers are hydrophilic and have historically been used in topsheets. For example, U.S. Pat. No. 6,548,731 to Mizutani, et al. teaches that relatively short hydrophilic fibers may be interspersed with longer hydrophobic fibers to form a topsheet material, and that hydrophobic synthetic fibers may be used if coated with a surfactant to make them hydrophilic. However, the surfactant will generally wash away when subjected to a large amount of liquid, thereby making the synthetic fibers hydrophobic again.

Although synthetic hydrophilic fibers such as rayon, viscose, acetate and spun nylon exist, these polymer types are generally relatively rigid and stiff, and many are difficult to extrude into thin fibers. Therefore, if such materials are used in fibers for a topsheet, the resulting topsheet would tend to be harsh and uncomfortable to the wearer of the absorptive device.

It is desirable to use less costly spun bonded nonwoven materials in absorptive devices and still deliver the softness of a typical spunlace nonwoven material.

SUMMARY

According to an aspect of the invention, there is provided a hydroformed expanded spun bonded nonwoven web having a first substantially planar surface on one side thereof and a second surface on an opposite side thereof. The second surface includes a plurality of protuberances in a pattern. The hydroformed expanded spun bonded nonwoeven web has an average loft of at least about 1.3 times greater than an original average loft of an original unexpanded spun bonded nonwoven web from which the hydroformed expanded spun bonded nonwoven web was created, and an air permeability of at least about 1.2 times greater than an original air permeability of the original unexpanded spun bonded nonwoven web.

In an embodiment, a basis weight of the hydroformed expanded spun bonded nonwoven web is substantially equal to an original basis weight of the original unexpanded spun bonded nonwoven web. In an embodiment, the basis weight is at least about 8 grams per square meter (gsm). In an embodiment, the basis weight is about 10 grams per square meter (gsm).

In an embodiment, an average loft of the original unexpanded spun bonded nonwoven web is between about 0.005 inch and about 0.025 inch when measured in cross-section by a magnifying optical device.

In an embodiment, an average air permeability of the original unexpanded spun bonded nonwoven web is about 1080 ft$^3$/ft$^2$/min and an average air permeability of the expanded spun bonded nonwoven web is about 1560 ft$^3$/ft$^2$/min when measured in an air permeability testing device.

In an embodiment, a plurality of substantially horizontal fibers of the hydroformed expanded spun bonded nonwoven web have a greater vertical spacing therebetween than a corresponding plurality of substantially horizontal fibers of the original unexpanded spun bonded nonwoven web.

In an embodiment, a plurality of fibers of the hydroformed expanded spun bonded nonwoven web are curved away from a substantially horizontal plane.

In an embodiment, the hydroformed expanded spun bonded nonwoven web includes a plurality of substantially horizontal continuous fibers and a plurality of fibrils, and each fibril is shorter than each continuous fiber.

In an embodiment, at least some of the plurality of the fibrils are oriented to a more vertical alignment as compared to the plurality of substantially horizontal continuous fibers.

In an embodiment, the hydroformed expanded spun bonded nonwoven web includes a surfactant. In an embodiment, the hydroformed expanded spun bonded nonwoven web includes a plurality of fibers, and the plurality of fibers include the surfactant.

According to an aspect of the invention, there is provided a hydroformed expanded spun bonded nonwoven web having a first substantially planar surface on one side thereof and a second surface on an opposite side thereof. The second surface includes a plurality of protuberances in a pattern. The hydroformed expanded spun bonded nonwoven web has a basis weight of about 10 grams per square meter (gsm) and a loft of at least about 0.009 inch.

According to an aspect of the present invention, there is provided a method for hydroforming a spun bonded nonwoven web. The method includes applying a plurality of pressurized liquid jets onto an outer surface of an original unexpanded spun bonded nonwoven web having an original loft while the original unexpanded spun bonded nonwoven web passes over a forming structure comprising a pattern of apertures and a vacuum slot area located beneath the forming structure to push and reorient a plurality of spun bonded fibers in the original unexpanded spun bonded nonwoven web from a closely packed substantially horizontal orientation to a more loosely packed orientation with greater vertical spacing between the fibers to produce a hydroformed expanded spun bonded nonwoven web having a loft of at least about 1.3 times greater than the original loft of the original unexpanded spun bonded nonwoven web, and an air permeability of at least about 1.2 times greater than an original air permeability of the original unexpanded spun bonded nonwoven web. The hydroformed expanded spun bonded nonwoven web has a first substantially planar surface on one side thereof and a second surface on an opposite side thereof. The second surface includes a plurality of protuberances in a pattern corresponding to the pattern of apertures in the forming structure.

In an embodiment, the hydroformed expanded spun bonded nonwoven web has an average loft of at least about 0.009 inch.

In an embodiment, the pressurized liquid jets having a pressure from about 200 psi to about 800 psi.

In an embodiment, the pressurized liquid jets produce a plurality of elongated ellipses of pressurized liquid, and each elongated ellipse has a length to width ratio of between about 3:1 and about 10:1. In an embodiment, each elongated ellipse has a length to width ratio of about 7:1.

In an embodiment, the forming structure includes a forming screen having a mesh count of between about 3 apertures per linear inch and about 120 apertures per linear inch. In an embodiment, the forming screen has a mesh count of between about 3 apertures per linear inch and about 40 apertures per linear inch.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The components of the following figures are illustrated to emphasize the general principles of the present disclosure and are not necessarily drawn to scale. Reference characters designating corresponding components are repeated as necessary throughout the figures for the sake of consistency and clarity.

DETAILED DESCRIPTION

Figure 1:
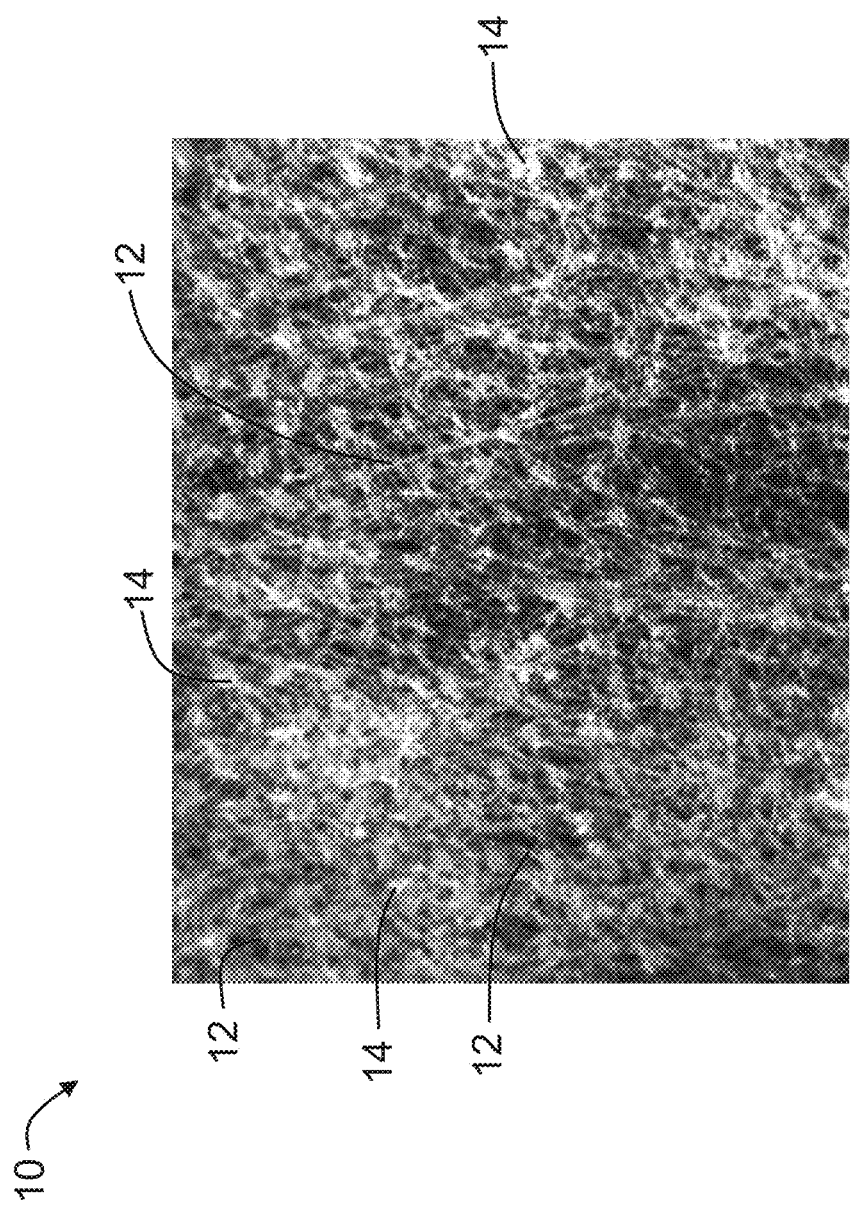
FIG. 1 is a microphotograph of an unexpanded spun bonded nonwoven of the prior art.

FIG. 1 is a top view of a portion of a spun bonded nonwoven web 10 having a basis weight of about 10 gsm. The nonwoven web 10 includes a plurality of fibers 12, and a plurality of compressed bond sites 14 that were created by a spun bonding process, as described above.

Figure 2:
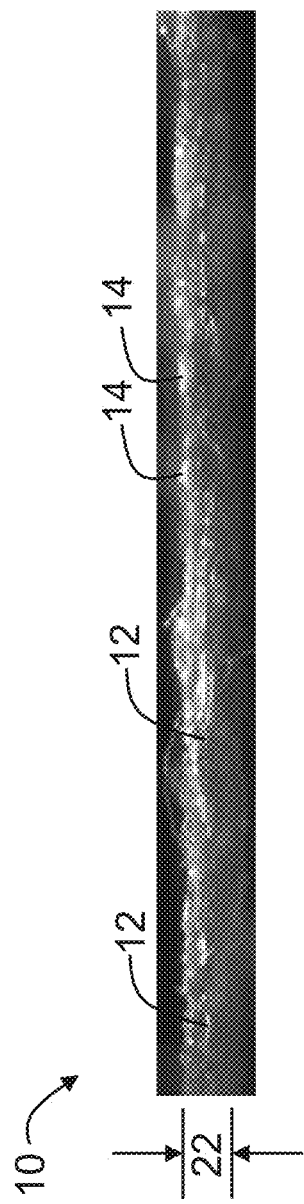
FIG. 2 is a microphotograph of a cross-section of the unexpanded spun bonded nonwoven of FIG. 1.

FIG. 2 illustrates a cross-section of the nonwoven web 10 of FIG. 1. As illustrated, the plurality of fibers 12 are generally oriented horizontally when the nonwoven web 10 is placed on a generally horizontal surface, i.e. each fiber lies in a plane that is generally horizontal and the fibers 12 are generally parallel to each other. The compressed bond sites 14 are also visible in FIG. 2. The fibers 12 are closely packed and therefore generally lack vertical spacing therebetween. The illustrated nonwoven web 10 has an average loft or thickness 22 of about 0.010 cm (0.0039 inch). Although a nominal 10 gsm spun bonded nonwoven web 10 is illustrated, embodiments of the invention are not so limited. The term "nominal" as used herein refers to an approximate value. For example, a nominal 10 gsm spun bonded nonwoven web may actually have an average basis weight of up to about 10.25 gsm. Spun bonded nonwoven webs having basis weights as low as nominal 8 gsm may be used in accordance with embodiments of the invention.

Although there may be no upper limit to the basis weight that may be used in embodiments of the invention, spun bonded nonwoven webs having a relatively high basis weight (and higher cost) may also have a higher loft and therefore may not be as desirable to use in embodiments of the invention. The illustrated embodiment is not intended to be limiting in any way. It is an aspect of embodiments of the invention to start with a light, inexpensive spun bonded nonwoven web and expand the web to simulate and function like a higher cost, lofty nonwoven web made with other processes, such as the spunlacing process described above.

The fibers 12 are made from polymer, which may be a polyolefin, such as polypropylene. In an embodiment, the nonwoven web 10 may be an SBPP, as described above. In an embodiment, the nonwoven web 10 may be coated with a surfactant so that the fibers 12 are hydrophilic on outer surfaces thereof. In an embodiment, a surfactant may be incorporated into the polymer of the fibers 12 in the form of a semi-viscous fluid that is located inside the polymer's amorphous regions so that the fibers 12 are hydrophilic and remain hydrophilic, even after the fibers 12 are subjected to liquids, as discussed in further detail below.

Figure 3:
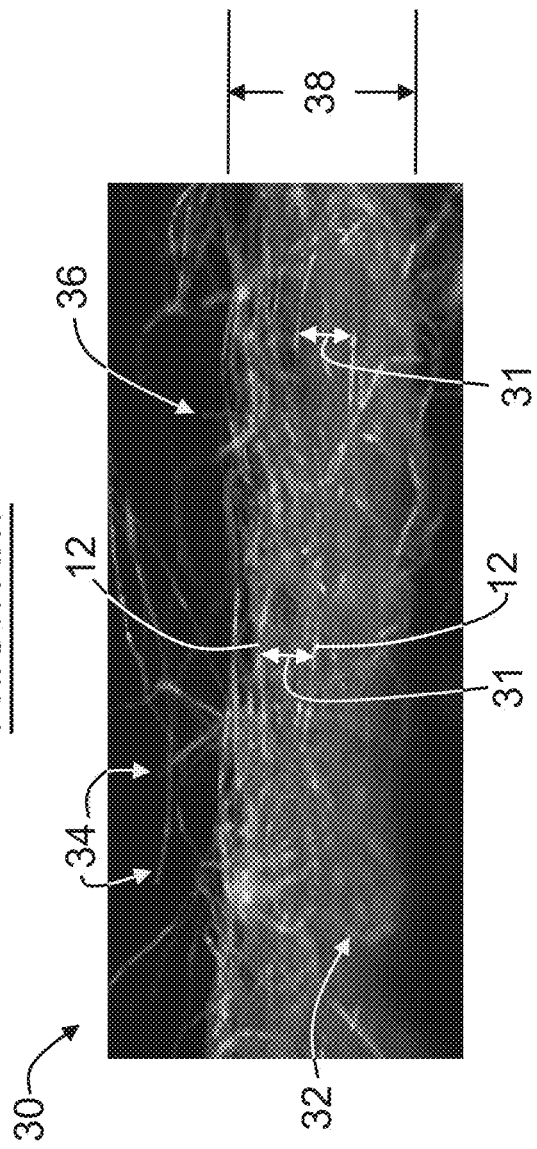
FIG. 3 is a microphotograph of a cross-section of a hydroformed expanded spun bonded nonwoven according to an embodiment of the invention.

FIG. 3 illustrates a cross-section of a portion of a hydroformed expanded spun bonded nonwoven web 30 that was hydroformed and expanded from the nonwoven web 10 illustrated in FIGS. 1 and 2 according to embodiments of the invention, described below. As illustrated, many of the fibers 12 of the original spun bonded nonwoven web 10 have been expanded to a greater vertical spacing therebetween, as indicated by arrows 31. During expansion of the nonwoven web 10, some of the fibers 12 may curve upward from their original generally horizontal orientations to become curved fibers 32. In addition, some of the fibers 12, which were previously continuous along the length of the nonwoven web 10, may break into shortened fibrils 34 during the expansion process, and at least some of the shortened fibrils 34 may be reoriented to a more vertical alignment and become substantially vertical fibrils 36, as illustrated.

The hydroformed expanded spun bonded nonwoven web 30 has an average expanded loft or thickness 38 of 0.050 cm (0.0197 inch), which is about 5.0 times greater than the original loft 22 of the original spun bonded nonwoven web 10. Embodiments of the invention provide an expanded spun bonded nonwoven web with a loft expanded to at least about 1.3 times the original spun bonded nonwoven web loft, which is sufficient for enhancing softness, for enhancing surface dryness, and for enhancing coolness as perceived by the wearer of an absorptive device that includes the hydroformed expanded spun bonded nonwoven web 30. In addition, the air permeability of the hydroformed expanded spun bonded nonwoven web 30 may be increased by at least about 1.2 times, as compared to the air permeability of the original spun bonded nonwoven web 10, as described in further detail below.

Figure 4:
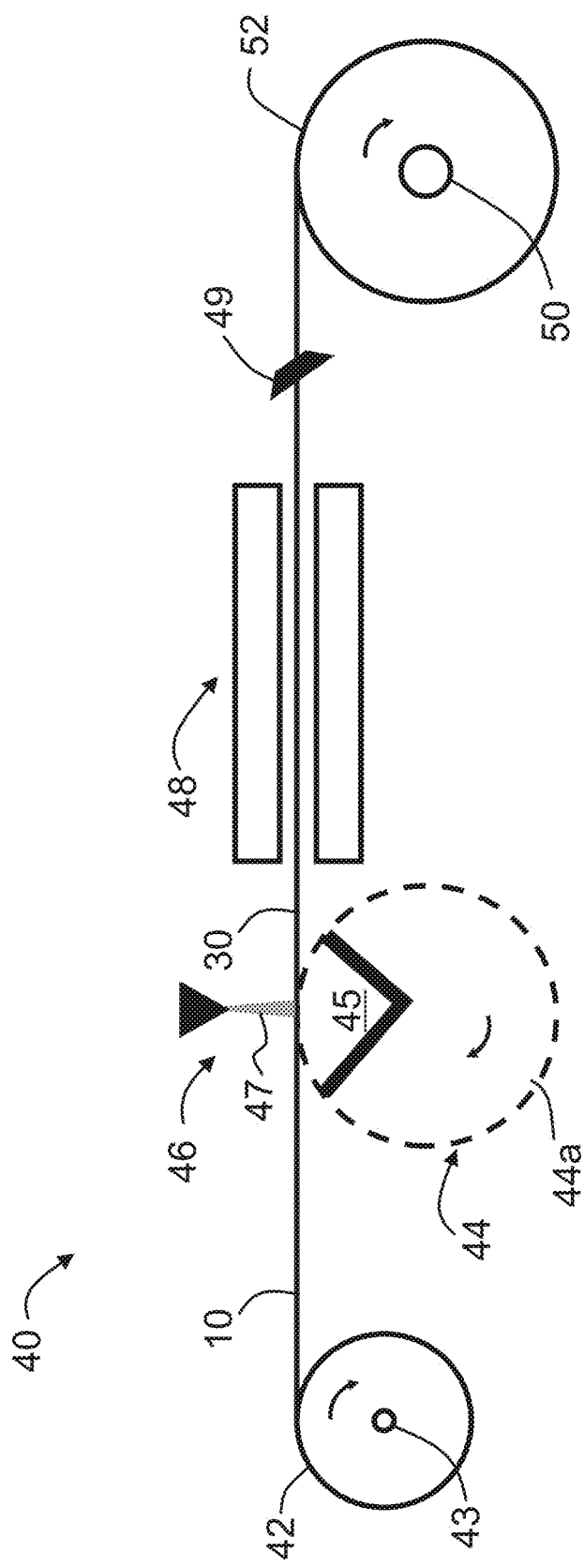
FIG. 4 is a schematic diagram of a hydroforming apparatus for carrying out methods according to embodiments of the invention.

FIG. 4 is a schematic side view of an embodiment of a hydroforming apparatus 40 for manufacturing a hydroformed expanded spun bonded nonwoven web, such as the hydroformed expanded spun bonded nonwoven web 30 described above and/or a hydroformed composite material described below, in accordance with embodiments of the invention. Specifically, the apparatus 40 of FIG. 4 provides a process of hydroforming a spun bonded nonwoven web, such as the spun bonded nonwoven web 10 illustrated in FIGS. 1 and 2 to expand its loft and produce a hydroforming expanded spun bonded nonwoven, such as the hydroformed expanded spun bonded nonwoven web 30 illustrated in FIG. 3.

As illustrated in FIG. 4, a roll 42 of an original unexpanded spun bonded nonwoven web 10 having an original loft as a result of the spun bonding process described above may be loaded on a spindle 43 of the apparatus 40 in an orientation and position that allows the nonwoven web 10 to be unwound from the roll 42 and further processed. The apparatus 40 includes a forming structure 44, which may be in the form of a rotatable forming screen, and the nonwoven web 10 may be advanced in a continuous motion over the forming structure 44. In embodiments in which the forming structure 44 is a rotatable forming screen, the nonwoven web 10 may be moved and the screen may be rotated at a synchronized speed across a long and narrow-width vacuum slot area 45 that extends into the paper containing the Figure. The forming structure 44 may have a plurality of apertures 44a having a mesh count of between about 3 apertures per linear inch (i.e. "3 mesh") and about 120 apertures per linear inch (i.e. "120 mesh"). In an embodiment, the mesh count may be about 25 apertures per linear inch (i.e. "25 mesh").

A plurality of pressurized liquid jets 46 is arranged in a long and narrow-width zone that extends into the paper containing FIG. 4, and is generally aligned with the long and narrow-width vacuum slot area 45 under the forming structure 44. The liquid jets 46 are configured to provide overlapping streams of a liquid 47, such as water, at a pressure of from about 200 psi to about 800 psi onto an outer surface of the nonwoven web 10 while the web 10 is passing over the vacuum slot area 45. In an embodiment, the liquid in the liquid jets 46 may have a pressure of from about 400 psi to about 800 psi. The streams of liquid 47 have sufficient pressure to push and reorient a majority of the spun bonded fibers 12 from a close packed horizontal orientation (illustrated in FIG. 2) to a greater vertical spacing (illustrated in FIG. 3).

Many of the fibers of the spun bonded nonwoven 10 may be pushed to curve upward and at least some of the formerly continuous fibers may be broken into shortened fibrils, as illustrated in FIG. 3. Such disruption of the original spun bonded nonwoven web 10 results in the expanded spun bonded nonwoven web 30 having an expanded loft of at least about 1.3 times greater than the loft of the original spun bonded nonwoven web 10, and an increased air permeability of at least about 1.2 times greater than the air permeability of the original spun bonded web. In addition, the liquid jets 46 have sufficient pressure to push portions of the nonwoven web 10 into the plurality of apertures 44a in the forming structure 44 and form a plurality of protuberances that extend from one surface of the expanded nonwoven web, as described in further detail below.

Figure 5:
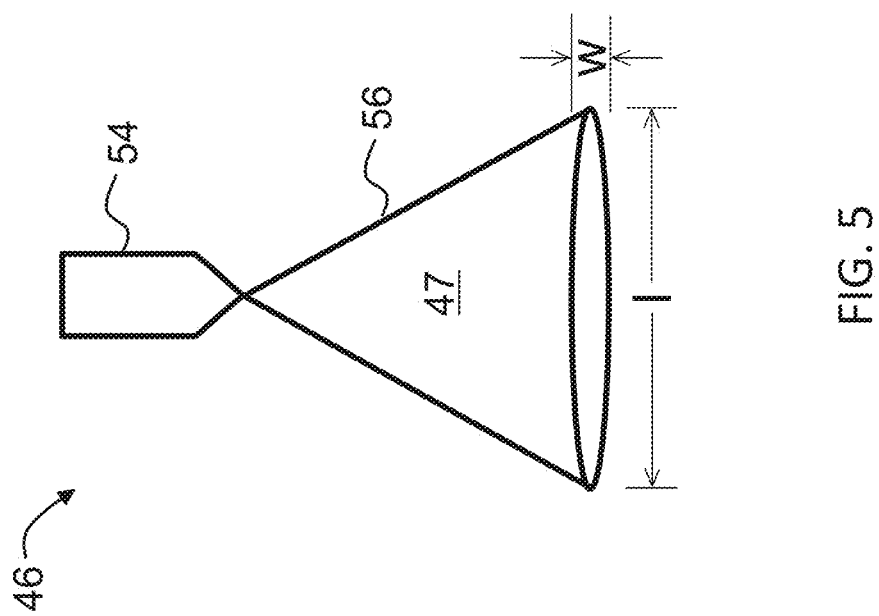
FIG. 5 is a schematic diagram of a pressurized jet of the hydroforming apparatus of FIG. 4.

FIG. 5 illustrates an individual liquid jet 46 in accordance with embodiments of the invention that may be used in the apparatus 40 of FIG. 4. As illustrated, the liquid jet 46 includes a nozzle 54 that is configured to project the stream of liquid 47 (such as water) that has a cross section in the shape of a fan. The stream of liquid 47 is generally shaped as an elongated ellipse having a width 'w' and a length 'l'. The stream of liquid 47 exiting an individual nozzle 54 may have an elongated ellipse shape having a length to width ratio (l/w) of between about 3:1 and about 10:1. In an embodiment, the stream of liquid 47 may have an elongated ellipse shape having a length to width ratio of about 7:1, with a length measuring about 1.75 inches and a width measuring about 0.25 inch at the location that impacts the nonwoven web 10.

Figure 6:
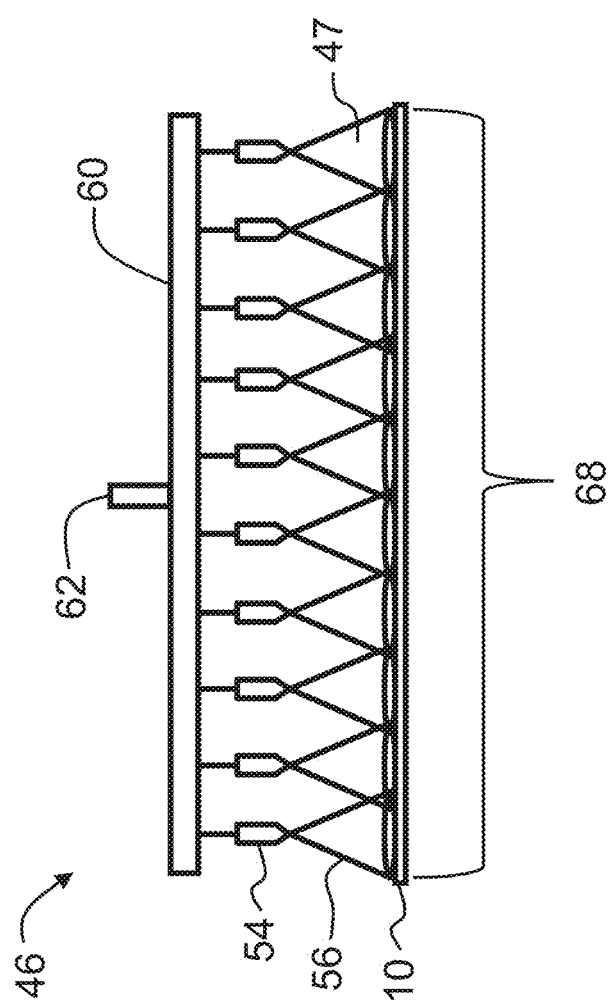
FIG. 6 is a schematic diagram of a plurality of pressurized jets of the hydroforming apparatus of FIG. 4.

The plurality of liquid jets 46 is illustrated in further detail in in FIG. 6. As illustrated, the individual nozzles 54 are aligned and affixed to a manifold 60 that is supplied with a pressurized liquid at an inlet 62. In an embodiment, the individual nozzles are spaced apart along the manifold 60 about every 1-2 inches. In an embodiment, the individual nozzles are spaced apart along the manifold about every 1.5 inches. The streams of liquid 47 each slightly overlap an adjacent stream at their respective edges 56. Together, the plurality of streams of liquid 47 produce a long and narrow-width zone of pressurized liquid 68 that is formed by the individual spray nozzles 54 that each shape the liquid into a respective elongated ellipse illustrated in FIG. 5. Edges 56 of the streams of liquid 47 overlap such that the pressurized liquid may be provided to the spun bonded nonwoven web 10 across the full width of the spun bonded nonwoven web 10, while maintaining a narrow width ('w' in FIG. 5), even as a collective.

Returning to FIG. 4, the vacuum slot area 45 may have sufficient suction to remove any residual liquid from the surface of the spun bonded nonwoven web that may reduce the force of the streams of liquid 47 striking the spun bonded nonwoven web 10. The expanded spun bonded nonwoven web 30 may then be subsequently dried in one or more dryers 48 and slit to preferred widths with at least one slitting blade 49. The expanded spun bonded nonwoven web 30 may be wound by a winder 50 into at least one roll 52. In an embodiment, the expanded spun bonded nonwoven web 30 may also be coated with a surfactant or otherwise treated to further enhance the properties of the expanded spun bonded nonwoven web 30.

As discussed above, in an embodiment, the fibers 12 may include a surfactant that may migrate to the outer surfaces of the fibers over time. Not to be bound by theory, the pressure differential between the pressure applied to surfactant fluid within the internal structure of the polymer of the fibers and the ambient atmosphere on the outside of the fibers will cause the surfactant to migrate toward the outside surfaces of the fibers until an equilibrium is achieved. It is suspected that only a small amount of the surfactant, which is incorporated in the polymer, migrates to the surface when achieving an equilibrium condition. If the surfactant is washed off of the surface of the fibers, either by the initial hydroforming process described above or by a liquid insult while being worn be a user, the equilibrium with be lost, and more surfactant will migrate towards the outer surfaces of the fibers to achieve a new equilibrium. The amount of surfactant to incorporate into the fibers may be determined in view of the amount expected to be lost during the hydroforming process, as well as during use of the absorptive device into which the fibers will be incorporated. If the hydroformed expanded nonwoven web 30 has a surfactant incorporated into the fibers thereof is used as, for example, a topsheet or an acquisition distribution layer ("ADL") in an absorptive device, the functional fluid acquisition rate value of the topsheet may continue to perform even after the absorptive device exceeds its fluid containment capacity.

Figure 7B:
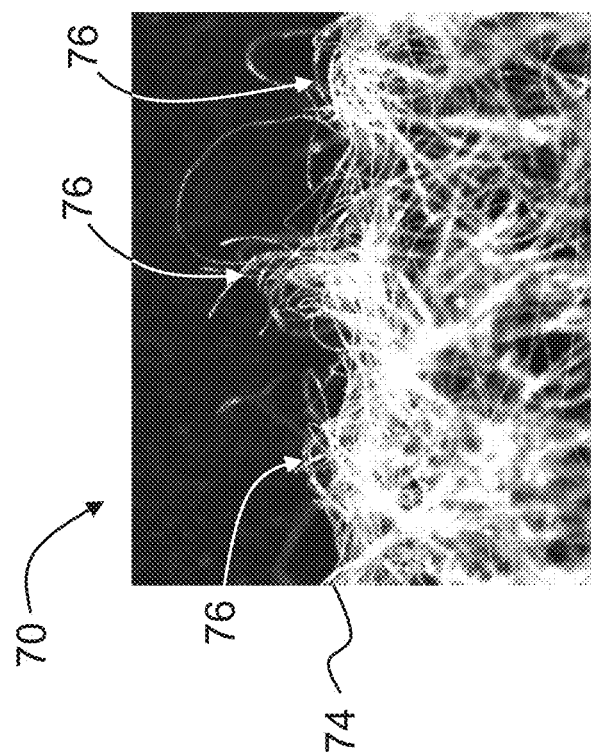
FIG. 7B is a microphotograph of a side view of a portion of another surface of the hydroformed expanded spun bonded nonwoven of FIG. 7A.
Figure 7A:
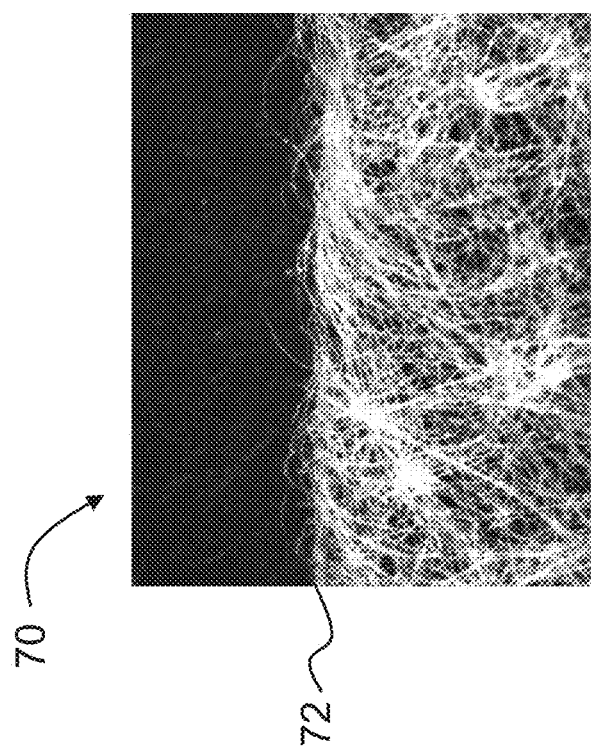
FIG. 7A is a microphotograph of a side view of a portion of one surface of a hydroformed expanded spun bonded nonwoven according to an embodiment of the invention.

FIGS. 7A and 7B are side views of a portion of a hydroformed expanded spun bonded nonwoven web 70 produced on a hydroforming apparatus, such as the apparatus 40 of FIG. 4. The hydroformed expanded spun bonded nonwoven web 70 was produced from an original spun bonded nonwoven web having a nominal basis weight of 10 gsm and an average loft or thickness of about 0.0040 inches (about 102 microns), as measured with an Ames 412.5 thickness gauge using a 4.8 ounce weight. FIG. 7A illustrates a first surface 72 of a first side of the hydroformed expanded spun bonded nonwoven web 70 that was subjected to the liquid jets 46 of the hydroforming apparatus 40, and FIG. 7B illustrates a second surface 74 of a second side of the hydroformed expanded spun bonded nonwoven web 70 that is opposite the first surface 72 and was in contact with the forming structure 44 of the hydroforming apparatus 40. As illustrated, the first surface 72 is substantially planar, while the second surface 74 has a pattern of protuberances 76 extending therefrom. The protuberances 76 are in substantially the same pattern as the pattern of apertures 44a in the forming structure 44, which has a mesh count of about 25 cells per linear inch (i.e. 25 mesh). The hydroformed expanded spun bonded nonwoven web 70 has an average loft or thickness of about 0.0076 inches (about 193 microns), as measured with an Ames 412.5 thickness gauge using a 4.8 ounce weight, or about 1.9 times (90%) greater than the loft of the original unexpanded spun bond nonwoven web.

Figure 8:
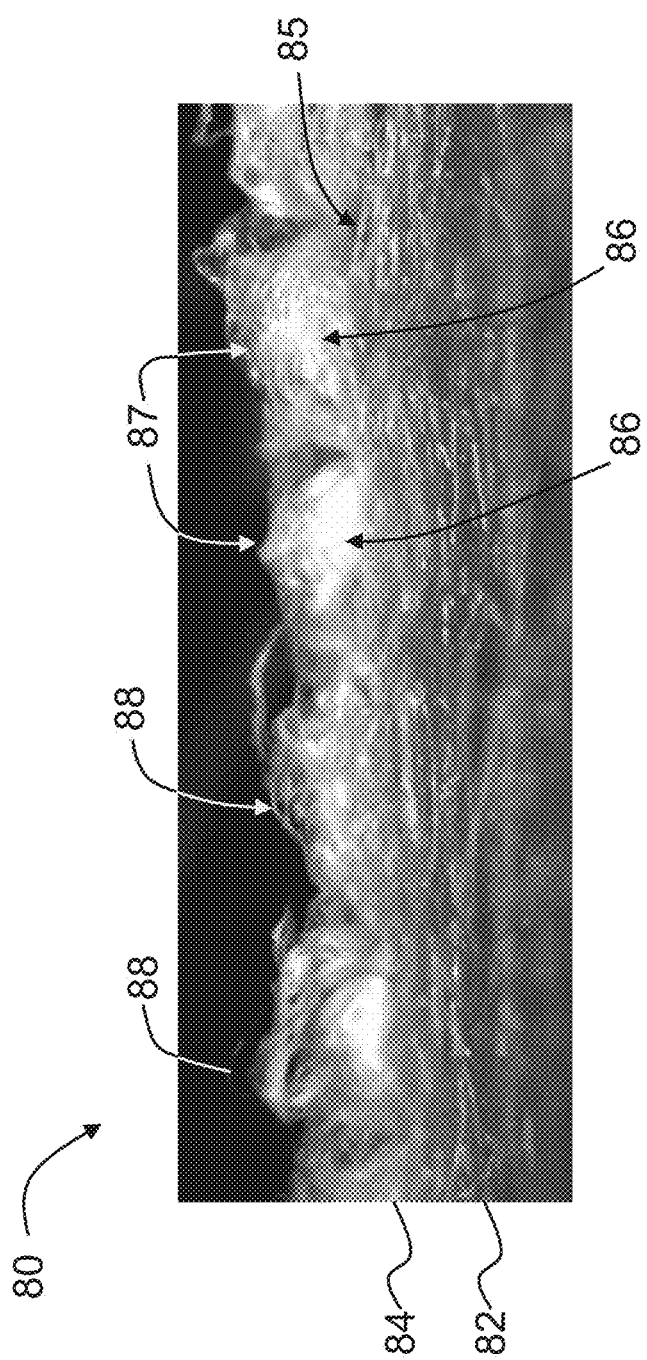
FIG. 8 is a microphotograph of a hydroformed composite material that includes an expanded spun bonded nonwoven layer and a polymer film layer according to an embodiment of the invention.

FIG. 8 illustrates a cross-section of a portion of a hydroformed composite material 80 that includes an expanded spun bonded nonwoven layer 82 and a polymer film layer 84. The film layer 84 includes a plurality of extended cells 86 that extend away from the expanded spun bonded nonwoven layer 82. In the illustrated embodiment, the extended cells 86 of the film layer 84 are each apertured at their respective apex 87, and the extended cells 86 are macro extended cells having a mesh count of about 25 cells per linear inch (i.e. "25 mesh"), which is substantially the same as the mesh count of the apertures 44a of the forming structure 44. The macro extended cells have sidewalls comprising a continually thinning portion of the hydroformed composite material extending away from what was an original plane of a composite precursor material (described below), and each of the plurality of extended cells is spaced apart from an adjacent extended cell by a land 85 having a width comprised of an undisturbed substantially planar surface of the hydroformed composite material. In the hydroformed composite material 80, fibers and fibrils from the expanded spun bonded nonwoven layer 82 have been pushed into the extended cells 86 of the film layer 84, and some of the fibrils 88 extend beyond a plane that contains the apexes 87 of the extended cells 86 of the film layer 84.

Figure 9:
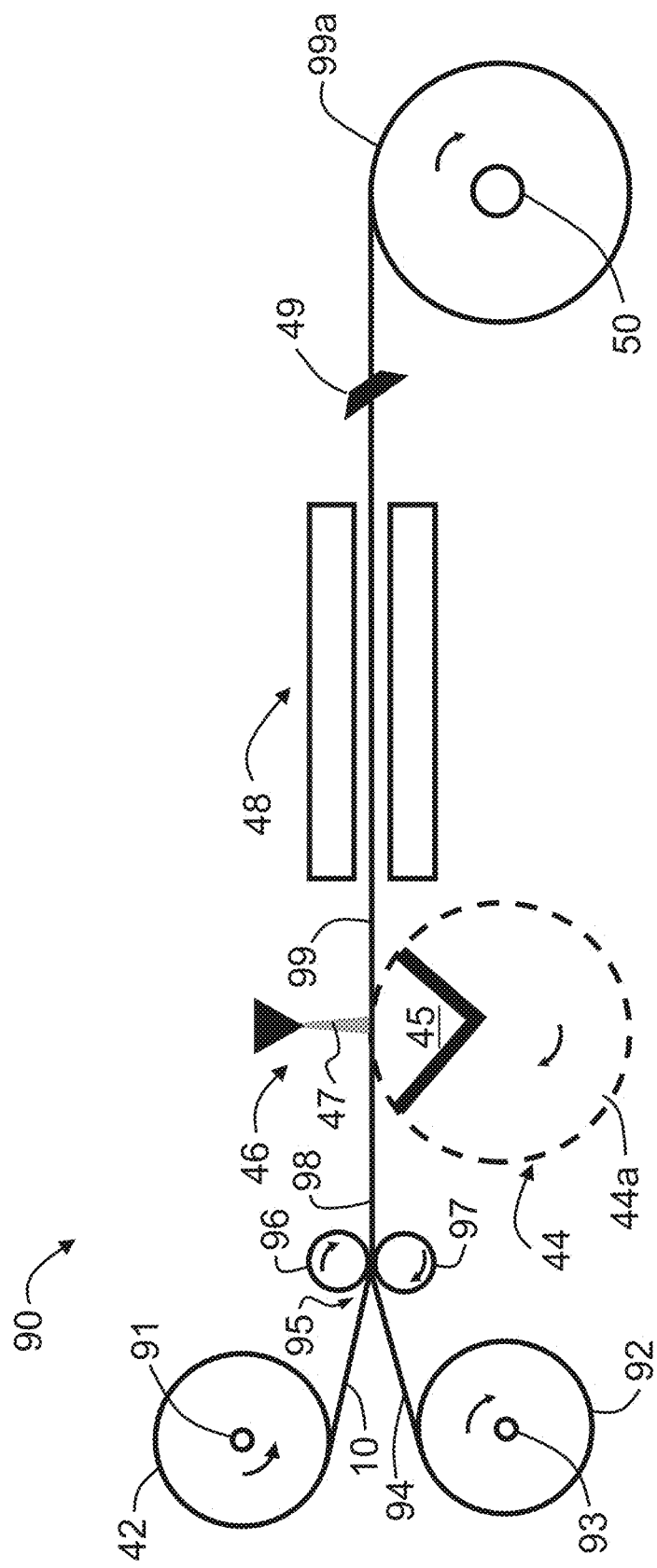
FIG. 9 is a schematic diagram of a lamination and hydroforming apparatus for carrying out methods according to embodiments of the invention.
Figure 10:
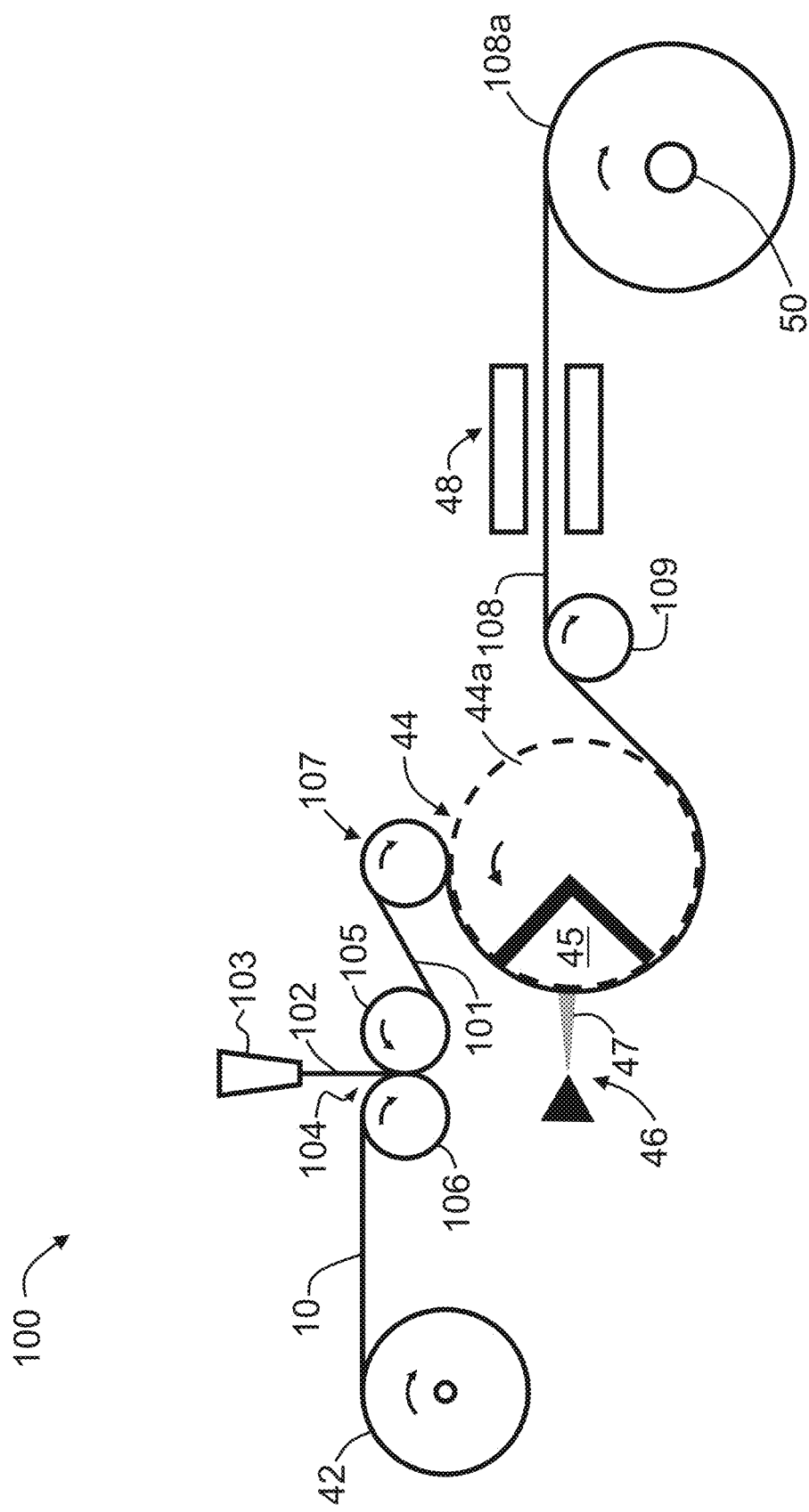
FIG. 10 is a schematic diagram of a lamination and hydroforming apparatus for carrying out methods according to embodiments of the invention.
Figure 11:
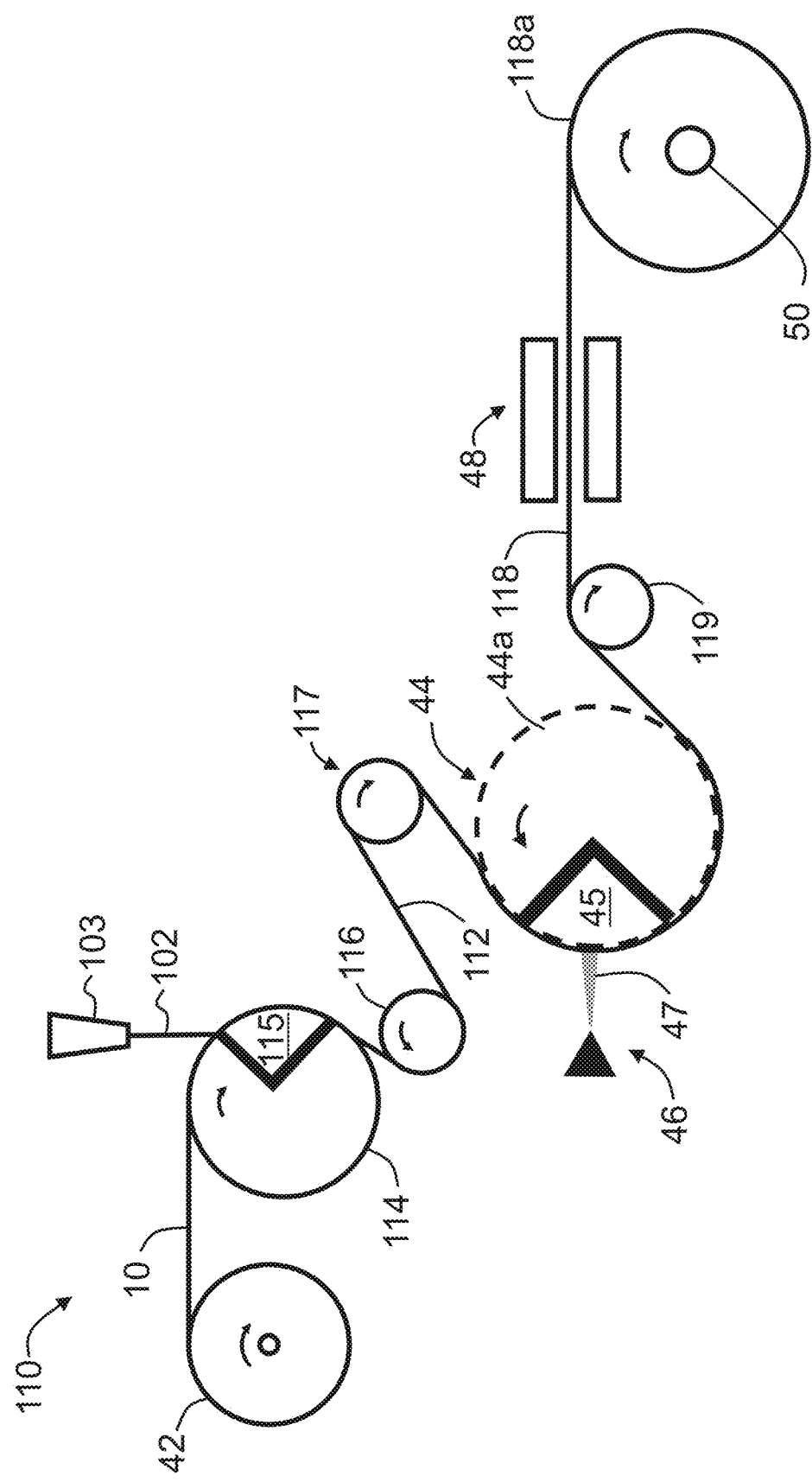
FIG. 11 is a schematic diagram of a lamination and hydroforming apparatus for carrying out methods according to embodiments of the invention.

A composite precursor material that is subjected to the hydroforming process may be created by different methods, as illustrated in FIGS. 9-11, for example. In an apparatus 90 illustrated in FIG. 9, the roll 42 of the original unexpanded nonwoven web 10 may be placed on a spindle 91, and a roll 92 of a polymer film 94 may be placed on a separate spindle 93. The polymer of the polymer film 94 may include one or more polyolefins, including but not limited to polyethylene, ultra-low density polyethylene, polypropylene, ethylene-vinyl acetates, metallocene, linear low density and linear medium density polyethylene, as well as other polymers, including but not limited to elastomeric polymers, including but not limited to polypropylene based elastomers, ethylene based elastomers, copolyester based elastomers, olefin block copolymers, styrenic block copolymers and the like, or combinations thereof. The polymer film 94 may be a solid polymer film or may be apertured. In an embodiment, the polymer film 94 may have a pattern of micro-cells or micro-apertures that were created using a vacuum forming, hydroforming, mechanical aperturing and/or embossing process.

Each of the original unexpanded nonwoven web 10 and the polymer film 94 may be fed into a nip 95 between two calendar rolls 96, 97, at least one of which may be heated to a temperature that allows the nonwoven web 10 and/or the polymer film 94 to soften. In an embodiment, at least one of the calendar rolls 96, 97 may have a three-dimensional pattern on its surface so that the polymer 94 film and the nonwoven web 10 are subjected to a point bonding process, as is known in the art. The pressure applied to the nonwoven web 10 and the polymer film 94 in the nip 95 allow the nonwoven web 10 and the polymer film 94 to adhere to each other to create a composite precursor material 98 prior to being subjected to the liquid jets 46 as the composite precursor material 98 comprising the nonwoven web 10 and the polymer film 94 passes over the forming structure 44. The combination of the liquid jets 46, the forming structure 44, and the vacuum slot 45 create a hydroformed composite material 99 that includes an expanded spun bonded nonwoven layer and a polymer film layer having extended cells in a pattern corresponding the pattern of apertures 44a in the forming structure, as described above with respect to the embodiment illustrated in FIG. 8. For example, if the forming structure 44 has a mesh count from about 40 apertures per linear inch (i.e. "40 mesh") to about 120 apertures per linear inch (i.e. "120 mesh"), then the hydroformed film cells will be extended micro-cells having a mesh count from about 40 mesh to about 120 mesh. If the forming structure has a mesh count of less than about 40 mesh, then the hydroformed film cells will be extended macro extended cells having a mesh count of less than about 40 mesh.

After passing through the dryer(s) 48, the hydroformed composite material 98 may be slit and rolled into a roll 99a with the winder 50. In an embodiment, at least the expanded spun bonded nonwoven layer of the hydroformed composite material 99 may also be coated with a surfactant or otherwise treated to further enhance the properties of the hydroformed composite material 99. In an embodiment, the fibers of the hydroformed composite material 99 may already contain a surfactant, as described above.

In an embodiment, the parts of the apparatus 90 located upstream of the liquid jets 46 and the forming structure 44 may be located off-line to form the composite precursor material 98, and a roll of the composite precursor material may be placed on the spindle 43 of the apparatus 40 of FIG. 4 and processed as described above.

FIG. 10 illustrates an embodiment of an apparatus 100 that is configured to create a laminated composite precursor material 101 by extruding a layer of molten polymer 102 from a film extrusion die 103 directly onto the original unexpanded spun bonded nonwoven web 10 at a nip 104 created by a metal roll 105 and a rubber roll 106 as the original unexpanded spun bonded nonwoven web 10 passes through the nip 104. The layer of molten polymer 102 may include one or more polyolefins, including but not limited to polyethylene, ultra-low density polyethylene, polypropylene, ethylene-vinyl acetates, metallocene, linear low density and linear medium density polyethylene, as well as other polymers, including but not limited to elastomeric polymers, including but not limited to polypropylene based elastomers, ethylene based elastomers, copolyester based elastomers, olefin block copolymers, styrenic block copolymers and the like, or combinations thereof.

A conveying roll 107 may be used to reorient the laminated composite precursor material 101 so that the polymer film layer of the laminated composite precursor material 101 contacts the forming structure 44 and the liquid jets 46 provide streams of liquid 47 directly onto the original spun bonded nonwoven web 10. It should be understood that additional rolls may be used in the apparatus 100 and the illustrated embodiment is not intended to be limiting in any way. The combination of the liquid jets 46, the forming structure 44, and the vacuum slot 45 create a hydroformed composite material 108 that includes an expanded spun bonded nonwoven layer and a polymer film layer having extended cells in a pattern corresponding the pattern of apertures 44a in the forming structure 44, as described above.

In the embodiment illustrated in FIG. 10, a conveying roll 109 is used to align the hydroformed composite material 108 with the dryer(s) 48, and after passing through the dryer(s) 48, the hydroformed composite material 108 may be slit and rolled into a roll 108a with the winder 50. In an embodiment, at least the expanded spun bonded nonwoven layer of the hydroformed composite material 108 may also be coated with a surfactant or otherwise treated to further enhance the properties of the hydroformed composite material 108. In an embodiment, the fibers of the hydroformed composite material 108 may already contain a surfactant, as described above.

It should be understood that additional rolls may be used to convey the hydroformed composite material 108 and the illustrated embodiment is not intended to be limiting in any way. In an embodiment, the parts of the apparatus 100 located upstream of the liquid jets 46 and the forming structure 44 may be located off-line to form the laminated composite precursor material 101, and a roll of the laminated composite precursor material may be placed on the spindle 43 of the apparatus 40 of FIG. 4 and hydroformed as described above.

FIG. 11 illustrates an embodiment of an apparatus 110 that is configured to create a laminated composite precursor material 112 by extruding the layer of molten polymer 102 from the film extrusion die 103 directly onto the original unexpanded spun bonded nonwoven web 10 as the original unexpanded spun bonded nonwoven web 10 moves over a second forming structure 114 at a synchronized speed so that the spun bonded nonwoven web 10 passes over a second vacuum slot area 115 as the molten polymer 102 contacts the nonwoven web 10. The second forming structure 114 has a pattern of apertures that are configured to allow the vacuum created in the second vacuum slot area 115 to pull the spun bonded nonwoven web 10 against the forming structure 114, and due to the permeability of the spun bonded nonwoven web 10, the polymer film layer will conform to the nonwoven web 10 as the polymer cools. Conveying rolls 116, 117 may be used to provide further cooling to the polymer layer and/or reorient the laminated composite precursor material 112 so that the polymer film layer of the laminated composite precursor material 112 contacts the forming structure 44 and the liquid jets 46 provide streams of liquid 47 directly onto the original spun bonded nonwoven web 10. It should be understood that additional rolls may be used to convey the composite precursor material 112 and the illustrated embodiment is not intended to be limiting in any way. The combination of the liquid jets 46, the forming structure 44, and the vacuum slot 45 create a hydroformed composite material 118 that includes an expanded spun bonded nonwoven layer and a polymer film layer having extended cells in a pattern corresponding the pattern of apertures 44a in the forming structure, as described above.

In the embodiment illustrated in FIG. 11, an additional conveying roll 119 is used to align the hydroformed composite material 118 with the dryer(s) 48, and after passing through the dryer(s) 48, the hydroformed composite material 118 may be slit and rolled into a roll 118a with the winder 50. In an embodiment, at least the expanded spun bonded nonwoven layer of the hydroformed composite material 118 may also be coated with a surfactant or otherwise treated to further enhance the properties of the hydroformed composite material 118. In an embodiment, the fibers of the hydroformed composite material 118 may already contain a surfactant, as described above.

It should be understood that additional rolls may be used to convey the hydroformed composite material 118 and the illustrated embodiment is not intended to be limiting in any way. In an embodiment, the parts of the apparatus 110 located upstream of the liquid jets 46 and the forming structure 44 may be located off-line to form the laminated composite precursor material 112, and a roll of the laminated composite precursor material 112 may be placed on the spindle 43 of the apparatus 40 of FIG. 4 and hydroformed as described above.

Other conventional processes may be used to create the composite precursor material and the processes described herein should not be considered to be limiting in any way. For example, in an embodiment, an adhesive material may be used to bond the polymer film and the original unexpanded spun bonded nonwoven web together. In an embodiment, an ultrasonic bonding device may be used to create bonds between the polymer film and the original unexpanded spun bonded nonwoven web.

A potential advantage of creating a laminated composite precursor material using a thermo-bonding process that includes extruding a layer of molten polymer directly onto the spun bonded nonwoven web, as described above with respect to FIGS. 10 and 11, is that the resulting polymer film layer may be thinner than processes that use an already-formed polymer film. For example, direct extrusion methods may allow for a very thin polymer film having a nominal basis weight of about 8-12 gsm.

The hydroformed expanded spun bonded nonwoven material having protuberances or the hydroformed composite material having extended cells (with or without apertures) may then be run a second time through the hydroforming process using the hydroforming apparatus 40 of FIG. 4 that includes a different forming structure 44 having a different mesh count of less than about 40 apertures per linear inch so that a pattern of macro protuberances or extended cells (with or without apertures) may be produced. The macro extended cells may have sidewalls that include a continually thinning portion of the hydroformed composite material extending away from an original plane of the hydroformed composite material. In an embodiment, the hydroforming apparatus 40 of FIG. 4 may be used to create a more three-dimensional surface by embossing the hydroformed composite material and not creating apertures.

Figure 12:
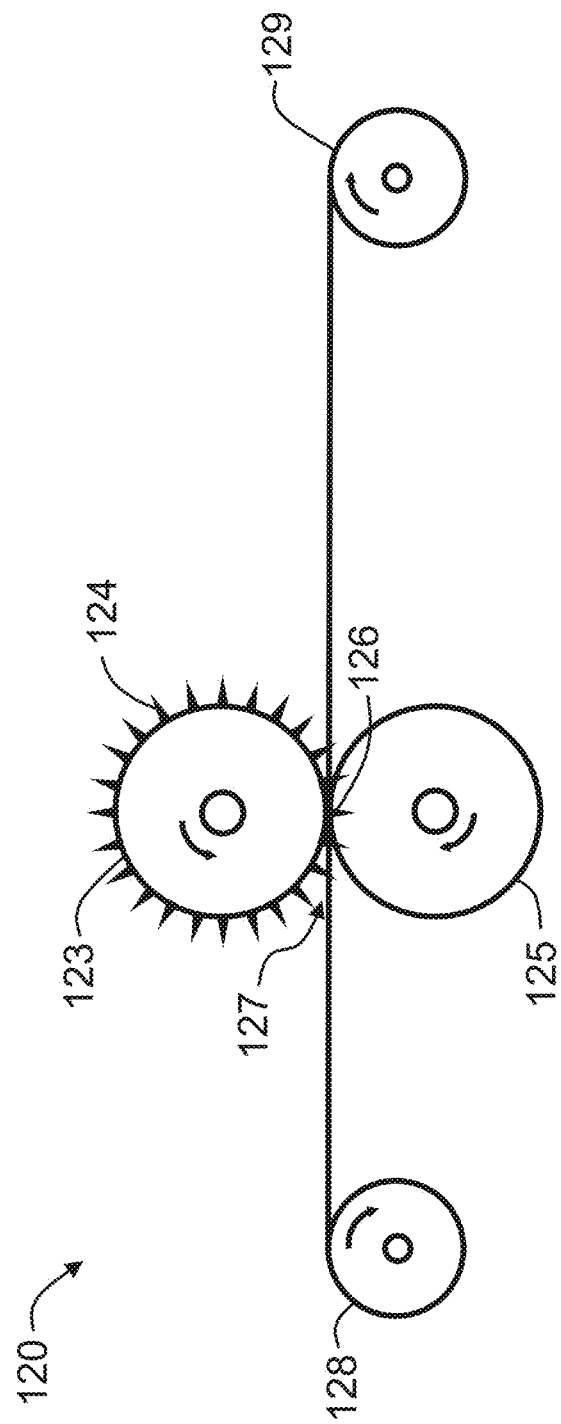
FIG. 12 is a schematic diagram of an apparatus for carrying out methods according to embodiments of the invention.

In an embodiment, a pattern of macro extended cells may be formed in the hydroformed expanded spun bonded nonwoven material or the hydroformed composite material already having protuberances or micro extended cells, respectively, via a method of mechanically perforating the material by passing the material through an apparatus configured to form large-scale apertures, such as an apparatus 120 illustrated FIG. 12. As illustrated, the apparatus 120 includes a pin roll 123 having a pattern of pins 124 and a counter roll 125 having a matching pattern of cavities 126 configured to receive the pins 124. The pin roll 123 and the counter roll 125 may be rotated in opposite directions to form a nip 127 through which a hydroformed composite material 128 may be fed. The pins 124 protrude from the surface of pin roll 123 and the cavities 126 are recessed into the surface of the counter roll 125. The pin roll 123 and the counter roll 125 may be aligned so that the pins 124 mate with the cavities 126 such that when the rolls 123, 125 are rotating, the pins 124 are inserted into the cavities 126 at the nip 127 and the hydroformed composite material 128 between the rolls 123, 125 is perforated by the pins 124, thereby forming a pattern of macro extended cells with apertures.

The resulting material includes micro extended cells (or protuberances) and macro extended cells with apertures and may be wound into a roll 129 for later conversion into a topsheet or other layer, such as an ADL, in an absorptive device. The macro extended cells may have a mesh count of less than about 40 cells per linear inch (i.e. "40 mesh"). The macro extended cells may extend away from the original plane of the hydroformed composite material, be spaced apart by lands that each has a width and comprised of a plane of the hydroformed composite material having micro extended cells. Such a mechanical perforation method is described in further detail in co-assigned U.S. Pat. No. 7,204,907 to Cree et al., the entire contents of which is incorporated herein by reference.

Figure 13:
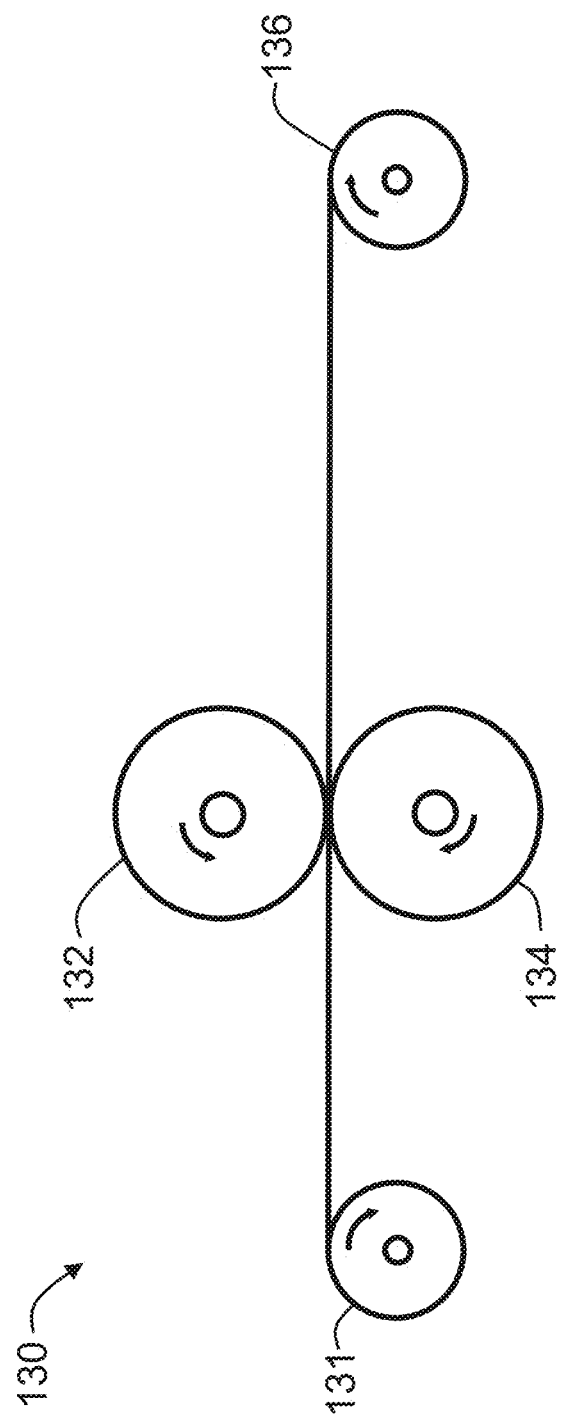
FIG. 13 is a schematic diagram of an apparatus for carrying out methods according to embodiments of the invention.

In an embodiment, a pattern of macro protuberances or macro extended cells may be formed in the hydroformed expanded nonwoven web and/or the hydroformed composite material using an apparatus 130 illustrated in FIG. 13. As illustrated, the pin roll 123 and the counter roll 125 of the apparatus 120 of FIG. 12 are replaced by matching embossing rolls 132, 134 so that a three-dimensional surface (without apertures) may be created on the hydroformed expanded spun bonded nonwoven material or the hydroformed composite material, represented by 131 in FIG. 13. After the material 131 passes between the embossing rolls 132, 134, the material may be rolled into a roll 136 for further processing.

In any of the methods described above for integrating macro extended cells (with or without apertures) into a hydroformed composite material with micro extended cells, if the hydroformed composite material is introduced to the process with the nonwoven layer oriented downward, the micro extended cells will be oriented upward and the macro extended cells will be oriented downward. Conversely, if the hydroformed composite material is introduced with the nonwoven layer oriented upward, the micro extended cells will be oriented downward and the macro extended cells will also be oriented downward. In an embodiment, a hydroformed composite material having macro extended cells of mesh counts of less than about 40 cells per linear inch may be further processed by one of the methods described above to add a second pattern of macro extended cells, although the smaller micro extended cells are desired for the land widths, because the micro extended cells may provide enhanced softness and/or offer capillary suction for enhanced surface dryness. Different combinations of micro extended cells (with or without apertures) and macro extended cells (with or without apertures), including the orientation of such extended cells may be created in accordance with embodiments of the invention. For example, using the apparatus described above, the size of the extended cells may be changed by changing the mesh pattern of the forming structure 44, and the orientation of the extended cells may be changed by changed by changing the orientation of the composite precursor material being fed onto the forming structure and/or the hydroformed composite material being fed into an apparatus for additional processing.

EXAMPLE 1

A spun bonded nonwoven web having a basis weight of 10.25 gsm (nominal 10 gsm) was processed using methods in accordance with embodiments of the invention over a variety of forming screens having mesh counts of greater than 40 apertures per linear inch, as well as mesh counts of less than 40 apertures per linear inch. The original loft of the spun bonded nonwoven averaged about 0.012 cm from a top surface to a bottom surface when measured in cross-section by a magnifying optical device that included a Navitar video imaging microscope with Image-Pro Plus® image analysis software. In an embodiment, the magnifying optical device may include a scanning electron microscope ("SEM"). Samples were each cut into about a 1.0 inch (2.54 cm) wide strip and then carefully shear cut across its width to minimize any compressive damage to the cross-section. The sample was then mounted with its edge upward toward the lens of the microscope. The image was focused and measured with line measurement provided by the software. Five spots were measured across the edge of the sample to determine an average loft for the sample. Multiple samples were tested from the same web. After processing the spun bonded nonwoven web using the method according to embodiments of the invention, the web expanded to an average of loft of 0.0267 cm with a standard deviation of 0.0053 cm, which was at least about 1.7 times the loft of the original spun bonded nonwoven web.

For at least one sample, a forming screen having a mesh count of 25 apertures per linear inch (i.e. "25 mesh") was used. More specifically, the forming screen had a pattern of nested pentagons that had an aperture measured from one flat side of the pentagon to its pointed top side of about 0.050 inch, and the apertures were spaced apart by lands having widths of about 0.007 inch. This expanded spun bonded nonwoven sample had a measured loft as high as 0.036 cm, which is an expansion of about 3.0 times the original loft of the spun bonded nonwoven web.

The 10.25 gsm spun bonded nonwoven web also had an original air permeability average of about 1080 cubic feet per square foot per minute ($ft^3/ft^2/min$), or about 329 cubic meters per square meter per minute ($m^3/m^2/min$), when measured in a device such as a Textest FX3300 Air Permeability Tester, which is the testing device used by the applicant for the data herein. After processing the spun bonded nonwoven web in accordance with embodiments of the invention on the same array of forming screens as described above, the air permeability increased to an average of about 1420 $ft^3/ft^2/min$, or 433 $m^3/m^2/min$, with a standard deviation of 120 $ft^3/ft^2/min$, or 37 $m^3/m^2/min$, which translates to an increased air permeability of at least about 1.2 times the air permeability of the original spun bonded web. When processed upon the aforementioned 25 mesh screen (i.e. a forming screen having a mesh count of 25 apertures per linear inch), the air permeability increased to as high as 1620 $ft^3/ft^2/min$, or 494 $m^3/m^2/min$, which translates to an increased air permeability of about 1.5 times the air permeability of the original spun bonded web.

EXAMPLE 2

The spun bonded nonwoven web was also hydroformed as part of a laminate (composite material) according to embodiments of the invention over an array of forming screens as described above. Such a hydroformed composite material should have enough integrity such that the layers will not peel apart and become separated, which may create converting issues when the hydroformed composite material is being constructed into an absorptive device. Even a very small amount of delamination force, i.e. the force that resists delamination of the two layers peeling apart, should be sufficient for most conversion processes. The hydroformed composite material according to embodiments of the invention exhibited a layer delamination force of at least about 3.0 grams when tested by a Peel Force Test Method that involves applying a piece of 2 inch wide masking tape of any brand to the nonwoven side of the composite material for a length of 8-10 inches, pulling the tape away from the film side for a distance of about 2-3 inches by hand, and placing the film and the tape in the jaws of any tensile test device common in the film industry. A jaw separation speed of 5 inches per minute may then activated, and the tensile testing device then calculates the average force experienced by the force gauge when the two layers are peeled apart. In some embodiments of the invention, the delamination force was measured to be as high as almost 20 grams.

By manipulating melt temperature and nip pressure in the aforementioned nip lamination process illustrated in FIGS. 10 and 11, the delamination force can be increased, but the laminating conditions should be balanced so that all the fibers of the nonwoven are not completely compressed into the polymer side of the composite precursor material. The vacuum lamination process illustrated in FIG. 11 may create a weaker bond (i.e. small delamination force), but still within the limits expressed herein and sufficient for most conversion processes. The materials according to embodiments of the invention are useful as layers in absorptive devices.

EXAMPLE 3-10

A nominal 10 gsm spun bonded nonwoven web having an average thickness of about 133 microns (0.0052 inch) and an average air permeability of about 311 m³/m²/min was hydroformed at different water pressures using a 43.5 mesh (43.5 apertures per linear inch) screen and a 60 mesh (60 apertures per linear inch) screen. Table I lists the resulting thicknesses and air permeabilities of the hydroformed nonwoven web using the 43.5 mesh screen at water pressures of 400 psi-550 psi, and Table II lists the resulting thicknesses and air permeabilities of the hydroformed nonwoven web using the 60 mesh screen at water pressures of 315 psi-500 psi.

TABLE I

Nonwoven Webs Hydroformed with 43.5 Mesh Screen

| Example | Water Pressure (psi) | Average Thickness (microns) | Average Air Permeability (m³/m²/min) |
|---|---|---|---|
| 3 | 400 | 192 | 391 |
| 4 | 450 | 191 | 418 |
| 5 | 500 | 205 | 422 |
| 6 | 550 | 218 | 475 |

Using the 43.5 mesh screen, the average thickness of the spun bonded nonwoven web was expanded to a thickness from about 1.44 times to about 1.64 times (i.e. about 44%-about 64%) greater than its original thickness, while the average air permeability increased from about 1.26 times to about 1.53 times (i.e. about 26%-53%) greater than its original air permeability, with the greatest increase in thickness and air permeability being obtained at the highest water pressure.

TABLE II

Nonwoven Webs Hydroformed with 60 Mesh Screen

| Example | Water Pressure (psi) | Average Thickness (microns) | Average Air Permeability (m³/m²/min) |
|---|---|---|---|
| 7 | 315 | 179 | 387 |
| 8 | 400 | 180 | 410 |
| 9 | 450 | 197 | 408 |
| 10 | 500 | 215 | 440 |

At each pressure, the average thickness of the spun bonded nonwoven web was expanded to a thickness from about 1.34 times to about 1.62 times (i.e. about 34%-about 62%) greater than its original thickness, while the average air permeability increased from about 1.24 times to about 1.42 times (i.e. about 24%-about 42%) greater than its original air permeability, with the greatest increase in thickness and air permeability being obtained at the highest water pressure.

Embodiments of the invention provide a hydroformed expanded spun bond nonwoven material with high loft for softness, and high air permeability for coolness and rapid fluid acquisition that may be suitable for a topsheet, i.e. a top layer that will contact the skin of the wearer of the absorptive device. Absorptive devices such as panty liners and feminine napkins may benefit from a cooler, softer topsheet. Embodiments of the invention also provide a hydroformed composite material with micro extended cells with apertures in the film layer that may be best suited for low fluid applications, such as panty liners. The film layer may add strength to the nonwoven material, as well as provide rewet performance enhancement, but without macro extended cells with apertures, the hydroformed composite material may not rapidly acquire high volumes of fluids. Therefore, using the hydroformed composites materials comprised of mesh counts higher than 40 cells per linear inch, i.e. micro extended cells, may be best suited for a precursor web to be introduced into processes described above that add macro extended cells, in accordance with embodiments of the invention.

After the macro extended cells have been integrated, the hydroformed composite material according to embodiments of the invention is especially soft and comfortable due the micro extended cells on the lands between the macro extended cells. The hydroformed composite material also has rapid fluid acquisition, which is desirable for use as a topsheet or an ADL in an absorptive device. The expanded spun bonded nonwoven material by itself may also be used as a topsheet in an absorptive device or in other applications that do not need a fluid barrier. If the hydroformed composite material has extended cells in the film layer that are not apertured, the hydroformed composite material may function as backsheet, because the un-opened cells would provide a fluid barrier while still providing the benefit of softness.

There are many applications in absorptive devices for hydroformed expanded spun bonded nonwoven materials and hydroformed composite materials in accordance with embodiments of the invention, as well as other types of devices that may benefit from the properties and performance provided by embodiments of the invention described herein. For example, embodiments of the invention may provide materials that are suitable for other absorptive devices, such as baby diapers or adult incontinence products, as well as wipes, cleansing devices, disposable clothing, and any other application that needs air and/or liquid permeability and high loft.

In an embodiment, the polymer film of the hydroformed composite material may be an elastomeric film and the hydroformed composite material that includes the elastomeric film and the expanded spun bonded nonwoven web may be used as a side panel, ear, leg cuff, waistband or the like in an absorptive device or any other product in which softness and stretch are desired.

The embodiments described herein represent a number of possible implementations and examples and are not intended to necessarily limit the present disclosure to any specific embodiments. Instead, various modifications can be made to these embodiments, and different combinations of various embodiments described herein may be used as part of the invention, even if not expressly described, as would be understood by one of ordinary skill in the art. Any such modifications are intended to be included within the spirit and scope of the present disclosure and protected by the following claims.

What is claimed is:

1. A method for hydroforming an original unexpanded spun bonded nonwoven web comprising a matt of entangled fibers held in place by a plurality of bonded points, the method comprising:

applying a plurality of pressurized liquid jets onto an outer surface of the original unexpanded spun bonded nonwoven web having an original loft while the original unexpanded spun bonded nonwoven web passes over a forming structure comprising a pattern of apertures and a vacuum slot area located beneath the forming structure to push and reorient a plurality of spun bonded fibers in the original unexpanded spun bonded nonwoven web from a closely packed substantially horizontal orientation to a more loosely packed orientation with greater vertical spacing between the fibers to produce a hydroformed expanded spun bonded nonwoven web having a loft of at least about 1.3 times greater than the original loft of the original unexpanded spun bonded nonwoven web, and an air permeability of at least about 1.2 times greater than an original air permeability of the original unexpanded spun bonded nonwoven web, wherein the hydroformed expanded spun bonded nonwoven web has a first substantially planar surface on one side thereof and a second surface on an opposite side thereof, the second surface comprising a plurality of protuberances in a pattern corresponding to the pattern of apertures in the forming structure.

2. The method according to claim 1, wherein the hydroformed expanded spun bonded nonwoven web has an average loft of at least about 0.009 inch.

3. The method according to claim 1, wherein the pressurized liquid jets having a pressure from about 200 psi to about 800 psi.

4. The method according to claim 1, wherein the pressurized liquid jets produce a plurality of elongated ellipses of pressurized liquid, each elongated ellipse having a length to width ratio of between about 3:1 and about 10:1.

5. The method according to claim 4, wherein each elongated ellipse has a length to width ratio of about 7:1.

6. The method according to claim 1, wherein the forming structure comprises a forming screen having a mesh count of between about 3 apertures per linear inch and about 120 apertures per linear inch.

7. The method according to claim 6, wherein the forming screen has a mesh count of between about 3 apertures per linear inch and about 40 apertures per linear inch.

* * * * *